(12) United States Patent
Haggerty et al.

(10) Patent No.: US 7,861,609 B2
(45) Date of Patent: Jan. 4, 2011

(54) APPARATUS FOR CONSTRUCTING A TARGET CORE FROM UNCONSOLIDATED SAND AND METHOD FOR USE OF SAME

(75) Inventors: Dennis Haggerty, Burleson, TX (US); John Douglas Manning, Alvarado, TX (US)

(73) Assignee: Halliburton Energy Services, Inc., Houston, TX (US)

(*) Notice: Subject to any disclaimer, the term of this patent is extended or adjusted under 35 U.S.C. 154(b) by 472 days.

(21) Appl. No.: 12/059,058

(22) Filed: Mar. 31, 2008

(65) Prior Publication Data

US 2009/0241700 A1  Oct. 1, 2009

(51) Int. Cl.
*G01D 21/00* (2006.01)
(52) U.S. Cl. ..................................... 73/866.5
(58) Field of Classification Search ................ 73/866.5
See application file for complete search history.

(56) References Cited

U.S. PATENT DOCUMENTS

| | | | |
|---|---|---|---|
| 2,705,418 | A | 4/1955 | Reichertz et al. |
| 3,934,455 | A | 1/1976 | Harrisberger |
| 4,253,327 | A | 3/1981 | Wiley |
| 4,562,726 | A | 1/1986 | Barnaby |
| 4,599,891 | A | 7/1986 | Brauer et al. |
| 4,616,134 | A | 10/1986 | Pruett et al. |
| 4,669,299 | A | 6/1987 | Closemann |
| 4,688,238 | A | 8/1987 | Sprunt et al. |
| 4,691,558 | A | 9/1987 | Vison et al. |
| 4,710,948 | A | 12/1987 | Withjack |
| 4,753,107 | A | 6/1988 | Reed et al. |
| 4,827,761 | A | 5/1989 | Vinegar et al. |
| 4,868,751 | A | 9/1989 | Dogru et al. |
| 5,025,669 | A | 6/1991 | Sarda et al. |
| 5,050,493 | A | 9/1991 | Prizio et al. |
| 5,065,421 | A | 11/1991 | Morineau et al. |
| 5,226,310 | A | 7/1993 | Steiger |
| 5,269,999 | A | 12/1993 | Smesny |
| 5,323,655 | A | 6/1994 | Eagan et al. |
| 5,325,723 | A | 7/1994 | Meadows et al. |
| 5,415,227 | A * | 5/1995 | Jennings, Jr. ............ 166/278 |
| 5,442,950 | A | 8/1995 | Unalmiser et al. |
| 5,637,796 | A | 6/1997 | Deruyter et al. |
| 5,868,030 | A | 2/1999 | Brumley et al. |

(Continued)

OTHER PUBLICATIONS

Ian C. Walton, et al.; "Perforating Unconsolidated Sands: An Experimental and Theoretical Investigation"; SPE Drilling and Completion, Sep. 2002.

(Continued)

*Primary Examiner*—Hezron Williams
*Assistant Examiner*—Rodney T Frank
(74) *Attorney, Agent, or Firm*—Lawrence R. Youst

(57) ABSTRACT

An apparatus for constructing a target core to enable testing at simulated wellbore conditions. The apparatus includes a support core having a target core receiving region. A flexible jacket is operable to receive the support core and apply a confining stress to the support core. A quantity of unconsolidated sand is disposed within the target core receiving region of the support core. The support core is operable to transmit at least a portion of the confining stress to the unconsolidated sand, thereby forming the target core. The apparatus simulates downhole conditions such that flow tests may be performed on the target core before and after perforating the target core.

25 Claims, 2 Drawing Sheets

U.S. PATENT DOCUMENTS

| | | |
|---|---|---|
| 5,969,227 A | 10/1999 | Kenney |
| 6,026,692 A | 2/2000 | Brovold |
| 6,055,874 A | 5/2000 | Onan et al. |
| 6,105,415 A | 8/2000 | Kenney |
| 6,401,523 B1 | 6/2002 | Fernandes et al. |
| 6,450,260 B1 * | 9/2002 | James et al. ............. 166/277 |
| 7,143,653 B2 | 12/2006 | Abdel-Hadi et al. |

OTHER PUBLICATIONS

European Search Report, EP 09 15 5986, European Patent Office, Nov. 30, 2009.

Kent Folse, et al.; "Perforating System Selection for Optimum Well Inflow Performance"; AAPG Annual Convention; Salt Lake City, Utah; May 11-14, 2003.

* cited by examiner

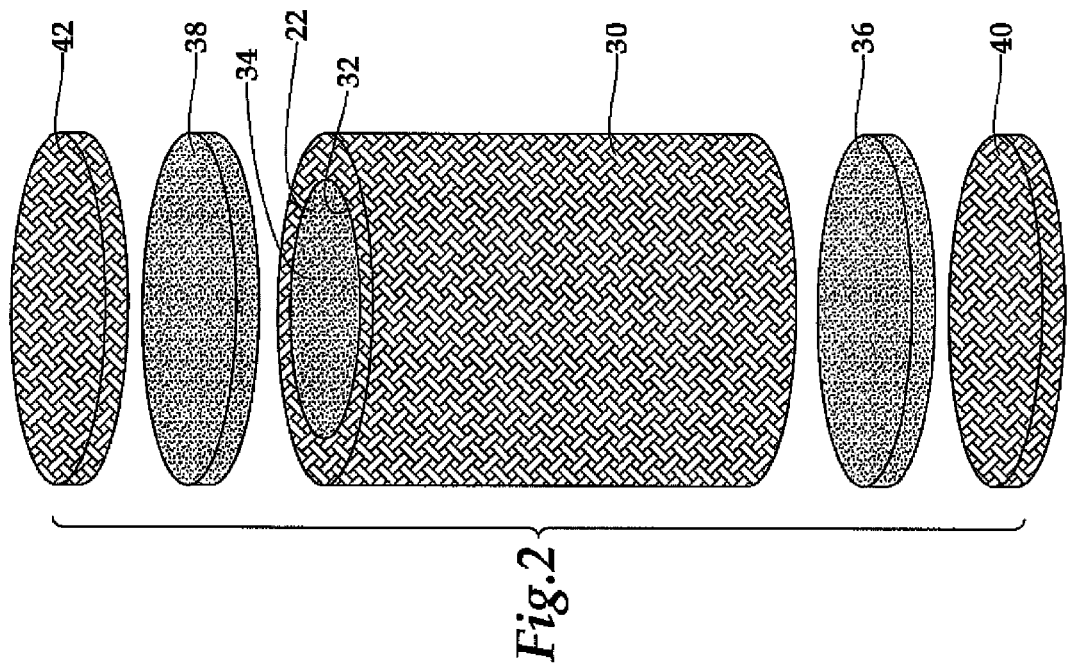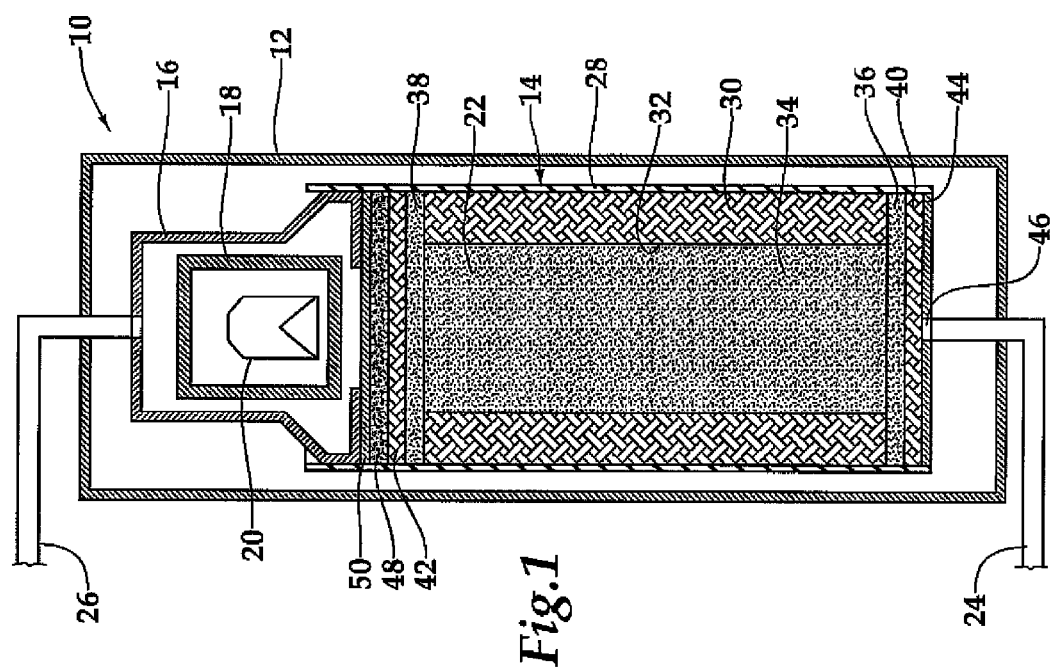

APPARATUS FOR CONSTRUCTING A TARGET CORE FROM UNCONSOLIDATED SAND AND METHOD FOR USE OF SAME

TECHNICAL FIELD OF THE INVENTION

This invention relates, in general, to testing and evaluation of unconsolidated sand and, in particular, to an apparatus for constructing a target core from unconsolidated sand that simulates downhole conditions and enables flow performance testing of a perforation made in the target core.

BACKGROUND OF THE INVENTION

Many factors associated with perforating a well may have an effect on the well productivity. Such factors include gun design including charge type, phasing, shot density, gun types and sizes; charge performance including penetration, hole size, tunnel geometry, gun standoff and eccentricity; conveyance method including tubing conveyed perforating, wireline, extreme overbalance and oriented guns; and reservoir characteristics including permeability, porosity, grain size, compressive strength, unconfined compressive strength, formation fluid type and completion fluid type.

Notwithstanding these numerous parameters, the selection of shaped-charge perforators for use in many completions is based solely on API Section I criteria. API Section I tests are designed to provide a simple means to assess charge penetration performance using standard field guns. The tests are conducted in concrete targets shot under surface conditions then the depth of penetration of the perforations is measured. Consequently, the natural conclusion is to assume that the largest penetration and/or exit hole size delivers the best productivity. Concerns have been raised, however, that charges can be designed to optimize performance in any material, and hence, comparison of performance in concrete targets may be misleading for selecting charges for rocks with different properties under difference conditions.

Accordingly, it would be beneficial to obtain data, such as penetration and inflow performance of given shaped charges, under in-situ conditions. Perforating procedures have been developed to evaluate well perforators under simulated in-situ conditions. For example, API Section IV provides a set of recommended procedures designed to assess performance of perforating gun systems under such conditions. Specifically, the Section IV test is designed to assess perforation inflow performance for a single shaped charge explosive under simulated in-situ stress and perforating conditions. While these procedures have existed since 1985, field validation of experimental results and model predictions based on these procedures have been limited.

Recently, however, a series of tests with Berea and Castlegate sandstone cores under varying in-situ conditions were conducted using these procedures. See "Perforating System Section for Optimum Well Inflow Performance," Kent Folse, et at. AAPG Annual Convention, May, 2003. In these tests, the sample target is perforated with a single shaped charge under in-situ stress and pore pressure conditions, and then, flowed to simulate well inflow performance. While the results of these experiments have been integrated with theoretical models and field data to improve well productivity for reservoirs in Berea and Castlegate sandstone, similar testing has not been achievable for unconsolidated sandstones due to an inability to simulate the in-situ stress and pore pressure conditions with unconsolidated sandstones. Accordingly, the benefits of Section IV testing and the associated improvements in well performance have not been extended to reservoirs in unconsolidated sandstones.

SUMMARY OF THE INVENTION

The present invention disclosed herein provides an apparatus for testing unconsolidated sand samples according to API Section IV procedures by enabling the construction of a target core formed from unconsolidated sand. According to the present invention, after the target core is constructed, it is placed in simulating downhole conditions for flow performance testing of a perforation made in the target core.

In one aspect, the present invention is directed to an apparatus for constructing a target core to enable testing at simulated wellbore conditions. The apparatus comprising a support core having a target core receiving region. A flexible jacket is operable to receive the support core and apply a confining stress to the support core. A quantity of unconsolidated sand is disposed within the target core receiving region of the support core. The support core is operable to transmit at least a portion of the confining stress to the unconsolidated sand, thereby forming the target core from the unconsolidated sand.

In one embodiment, the support core, the target core and the flexible jacket are each substantially cylindrical. In another embodiment, the support core is formed from a consolidated sandstone such as Castlegate sandstone, Berea sandstone or synthetic sandstone that may be formed from cement. In this embodiment, the support core may have a compressive strength between about 1,000 psi and about 12,000 psi. In a further embodiment, the flexible jacket may be constructed from a rubber sleeve. In another embodiment, the confining stress is a radial confining stress created by applying pressure to the exterior of the flexible jacket.

In one embodiment, the apparatus may also include first and second unconsolidated sand layers and first and second end plates positioned at first and second ends of the support core. The first and second unconsolidated sand layers, respectively, are in contact with first and second ends of the target core. In this embodiment, the first and second end plates may be formed from the same material as the support core. This embodiment may also include a flow distributor plate positioned adjacent to the first end plate and opposite the first unconsolidated sand layer, a cement coupon positioned adjacent to the second end plate and opposite the second unconsolidated sand layer and a casing plate positioned adjacent to the cement coupon and opposite the second end plate. Once in this configuration, an axial confining stress may be applied to the target core created by applying pressure to the casing plate and the flow distributor plate. Further, a gun assembly may be operably positioned relative to the casing plate. The gun assembly includes a shaped charge operable to form a perforation in the target core under the simulated downhole conditions.

In another aspect, the present invention is directed to an apparatus for constructing a target core to enable testing at simulated wellbore conditions that includes a support core having a target core receiving region and first and second ends, a flexible jacket operable to receive the support core and apply a confining stress to the support core and a quantity of unconsolidated sand disposed within the target core receiving region of the support core. First and second unconsolidated sand layers are positioned at the first and second ends of the support core such that the first and second unconsolidated sand layers, respectively, contact first and second ends of the unconsolidated sand disposed within the target core receiving region. First and second end plates are positioned adjacent to the first and second unconsolidated sand layers. The apparatus also includes a flow distributor plate positioned adjacent to the first end plate and opposite the first unconsolidated sand layer, a cement coupon positioned adjacent to the second end plate and opposite the second unconsolidated sand layer and a casing plate positioned adjacent to the cement coupon and opposite the second end plate. A gun assembly is operably positioned relative to the casing plate, wherein the gun assembly including a shaped charge. In this configuration, the support core is operable to transmit at least a portion of the confining stress to the unconsolidated sand thereby forming the target core from the unconsolidated sand such that detonation of the shaped charge to form a perforation in the target core occurs under the simulated downhole conditions.

In a further aspect, the present invention is directed to a method for constructing a target core to enable testing at simulated wellbore conditions. The method includes providing a support core having a target core receiving region, positioning the support core in a flexible jacket, disposing a quantity of unconsolidated sand within the target core receiving region of the support core, applying a confining stress to the support core and transmitting at least a portion of the confining stress to the unconsolidated sand thereby forming the target core from the unconsolidated sand.

In yet another aspect, the present invention is directed to a method for perforating a target core at simulated wellbore conditions. The method includes providing a support core having a target core receiving region, positioning the support core in a flexible jacket, disposing a quantity of unconsolidated sand within the target core receiving region of the support core, applying a confining stress to the support core, transmitting at least a portion of the confining stress to the unconsolidated sand thereby forming the target core from the unconsolidated sand and detonating a shaped charge positioned relative to the target core to form a perforation in the target core under the simulated downhole conditions.

In still another aspect, the present invention is directed to a method for performance testing of a perforation in a target core at simulated wellbore conditions. The method includes providing a support core having a target core receiving region, positioning the support core in a flexible jacket, disposing a quantity of unconsolidated sand within the target core receiving region of the support core, applying a confining stress to the support core, transmitting at least a portion of the confining stress to the unconsolidated sand thereby forming the target core from the unconsolidated sand, flowing a first fluid sample axially through the target core, detonating a shaped charge positioned relative to the target core to form a perforation in the target core under the simulated downhole conditions and flowing a second fluid sample axially through the target core. In this method, measured parameters associated with flowing the first fluid sample and the second fluid sample are compared to determine flow performance of the perforation.

BRIEF DESCRIPTION OF THE DRAWINGS

For a more complete understanding of the present invention, including its features and advantages, reference is now made to the detailed description of the invention, taken in conjunction with the accompanying drawings in which like numerals identify like parts and in which:

FIG. 1 is a schematic illustration of an apparatus for constructing a target core to enable testing at simulated wellbore conditions embodying principles of the present invention;

FIG. 2 is an exploded view of certain components of an apparatus for constructing a target core to enable testing at simulated wellbore conditions embodying principles of the present invention;

DETAILED DESCRIPTION OF THE INVENTION

Figure 4:
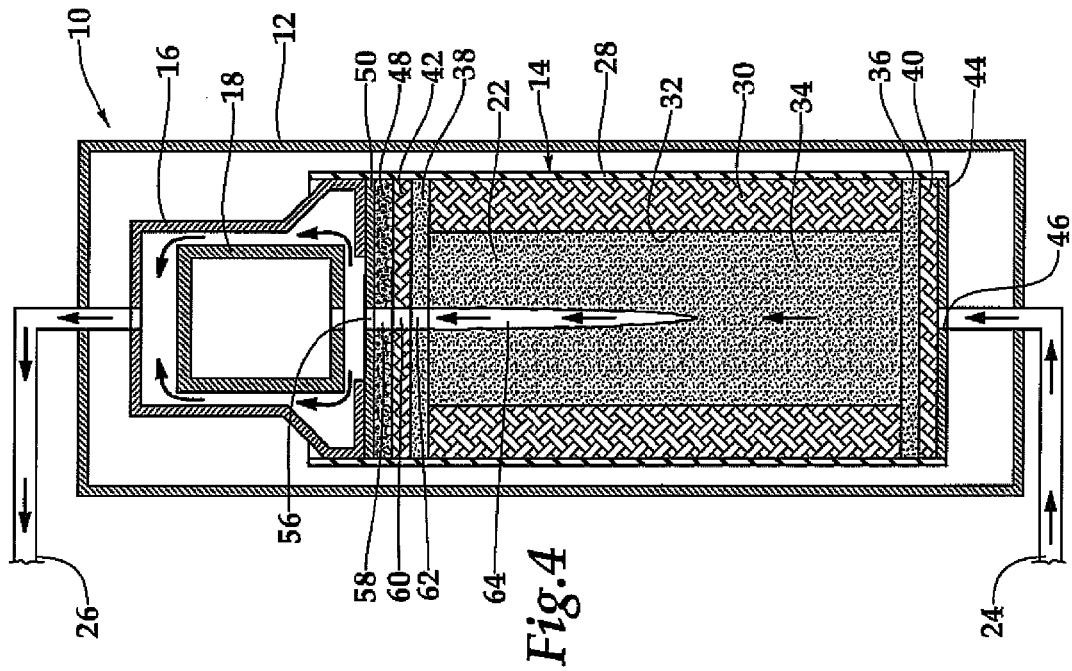
FIG. 4 is a schematic illustration of an apparatus for constructing a target core to enable testing at simulated wellbore conditions embodying principles of present invention in a flow test configuration after rating the target core.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the invention.

Referring initially to FIG. 1, therein is representatively illustrated an apparatus for constructing a target core to enable testing at simulated wellbore conditions embodying principles of the present invention that is generally designated 10. Apparatus 10 includes a pressure vessel 12 that is operable to be pressurized to a desired pressure such as between about 2,000 psi and about 10,000 psi to provide a confining pressure on the target assembly 14. It will be understood by those skilled in the art that other pressures both lower and higher than those specified are also considered to be within the scope of the present invention.

Apparatus 10 includes a simulated wellbore 16 that contains a perforating gun assembly 18 including a shaped charge 20. Simulated wellbore 16 is operable to be pressurized to a desired pressure such as between about 500 psi and 5,000 psi, however, factors such as whether perforating will take place in an underbalance condition, an overbalance condition, an extreme overbalance condition or the like will determine the desired pressure. Shaped charge 20 may be any desired oil field shaped charge including, for example, a shaped charge taken from a minimum production run of 1,000 RDX, HMX, HNS, PYX or similar explosive containing charges and packaged in the manufacturing company's standard shipping containers. Also, preferably, shaped charge 20 will be allowed to age for at least four weeks prior to its use in apparatus 10.

Apparatus 10 includes a flow system for applying pore pressure to the target core 22. The pore pressure may be any desired pressure such as between about 500 psi and 5000 psi. In the illustrated embodiment, only the inlet tubing 24 and outlet tubing 26 of the flow system are depicted. It will be understood by those skilled in the art that a suitable flow system will also included one or more pumps, one or more filters or filter stages, a heating element and the like, as well as a variety of sensors including flow sensors, pressure sensors, temperature sensors and the like. The fluid that is pumped through the flow system is preferably a mineral spirits but may be any desired fluid including a brine such as a sodium chloride solution or a mixture of an oil and a brine solution.

Target assembly 14 includes a flexible jacket 28 that may be formed from a rubber or other polymeric or resilient material. Preferably, flexible jacket 28 is substantially cylindrical in shape. Disposed within flexible jacket 28 is a support core 30. Support core 30 is preferably formed from a material having a moderate unconfined compressive strength such as a consolidated sandstone. Suitable consolidated sandstones include Castlegate sandstone and Berea sandstone. Alternatively, support core 30 may be formed from a synthetic sandstone that is constructed to the desired specifications from a cement mixture. Support core 30 preferably has a compressive strength between about 1,000 psi and about 12,000 psi but those skilled in the art will understand that other compressive strengths both lower and higher than those specified are also considered to be within the scope of the present invention. As best seen in FIG. 2, support core 30 is substantially cylindrical in shape and defines a substantially cylindrical target core receiving region 32. In certain embodiments, support core 30 may have an outer diameter of about seven inches and target core receiving region 32 may have a four and one half inch diameter, however, other diameters, both larger and smaller, for both support core 30 and target core receiving region 32 are possible and are considered within the scope of the present invention. Preferably, support core 30 has a near-matching texture and similar compressive properties that converge with that of target core 22 as stress is increased.

Target assembly 14 further includes a quantity of unconsolidated sand 34 disposed within target core receiving region 32 of support core 30. Unconsolidated sand 34 preferably has a compressive strength between about 0 psi and about 1,000 psi but those skilled in the art will understand that the compressive strength of unconsolidated sand 34 be higher than 1,000 psi while still remaining within the scope of the present invention. In one embodiment, unconsolidated sand 34 is in the form of a sand mix slurry that may be packed into target core receiving region 32 of support core 30. Unconsolidated sand 34 may be obtained from a core sample of the reservoir formation of interest. Alternatively, unconsolidated sand 34 may be formed from a sand having a mineralogical composition that matches or is similar to that of the reservoir formation of interest, for example, a sand having similar grain size and density as the reservoir formation of interest and may include additives such as quartz sand, clays such as Bentonite or the like.

Target assembly 14 also includes two unconsolidated sand layers 36, 38 that are positioned, respectively, above and below unconsolidated sand 34 and support core 30. Unconsolidated sand layers 36, 38 are preferably formed from the same mixture as unconsolidated sand 34, however, unconsolidated sand layers 36, 38 may alternative be formed from a mixture have different constituents. Unconsolidated sand layers 36, 38 are preferably between about half an inch and two inches thick, but may be either thicker or thinner than specified while remaining within the scope of the present invention. Above and below unconsolidated sand layers 36, 38 are end plates 40, 42. End plates 40, 42 are preferably formed from the same material as support core 30, however, end plates 40, 42 may alternative be formed from a different material. End plates 40, 42 are preferably between about one quarter of an inch and one inch thick, but may be either thicker or thinner than specified while remaining within the scope of the present invention.

Below end plate 40, target assembly 14 includes a flow distributor plate 44. Flow distributor plate 44 is preferably formed from a metal such as steel. Flow distributor plate 44 is provides an interface between target assembly 14 and the flow system such that fluid from the flow system may enter target assembly 14 via opening 46. At its upper end, target assembly 14 includes a cement coupon 48 that is preferably a three quarter inch neat cement or equivalent. Those skilled in the art, however, will understand that other materials with other thicknesses may alternatively be used and would be considered to be within the scope of the present invention such materials and thicknesses may be selected to best match that of the wellbore associated with the reservoir formation being simulated. Also at the upper end of target assembly 14 is a casing plate 50. Casing plate 50 is preferably, a one half inch ASTM 4140 steel or equivalent plate, however, those skilled in the art will understand that other materials with other thicknesses may alternatively be used and would be considered to be within the scope of the present invention such materials and thicknesses may be selected to best match that of the wellbore associated with the reservoir formation being simulated.

The construction of an example target core 22 will now be described. A core, for example a seven inch cylindrical core, is cut from a desired material such as Castlegate sandstone as the first step in forming support core 30. An inner core, for example a four and a half inch cylindrical core, is then cut out of the center of support core 30 to form target core receiving region 32. Support core 30 is then allowed to dry. Also cut from the Castlegate sandstone, are end plates 40, 42, which are preferably one half inch in thickness and seven inches in diameter. A quantity of unconsolidated sand 34 is then prepared. In one example, unconsolidated sand 34 contains 87.43 percent by weight of Oklahoma #1, 9.93 percent by weight crushed Castlegate sandstone and 1.98 percent by weight Bentonite. These ingredients are combined together dry then mixed with 0.66 percent by weight potassium chloride in a 3% solution.

Once support core 30 is dry and unconsolidated sand 34 is prepared, target assembly 14 may be assembled. End plate 40 is placed on flow distributor plate 44. An unconsolidated sand layer 36, preferably about one inch thick, is placed on end plate 40. Support core 30 is disposed within flexible jacket 28 and this assembly is placed on unconsolidated sand layer 36. Target core receiving region 32 is now packed with unconsolidated sand 34. Once target core receiving region 32 is full of unconsolidated sand 34, an additional quantity of unconsolidated sand is placed on top of support core 30 and unconsolidated sand 34 to form unconsolidated sand layer 38, which is preferably one inch thick. End plate 42 is then placed on unconsolidated sand layer 38.

Figure 3:
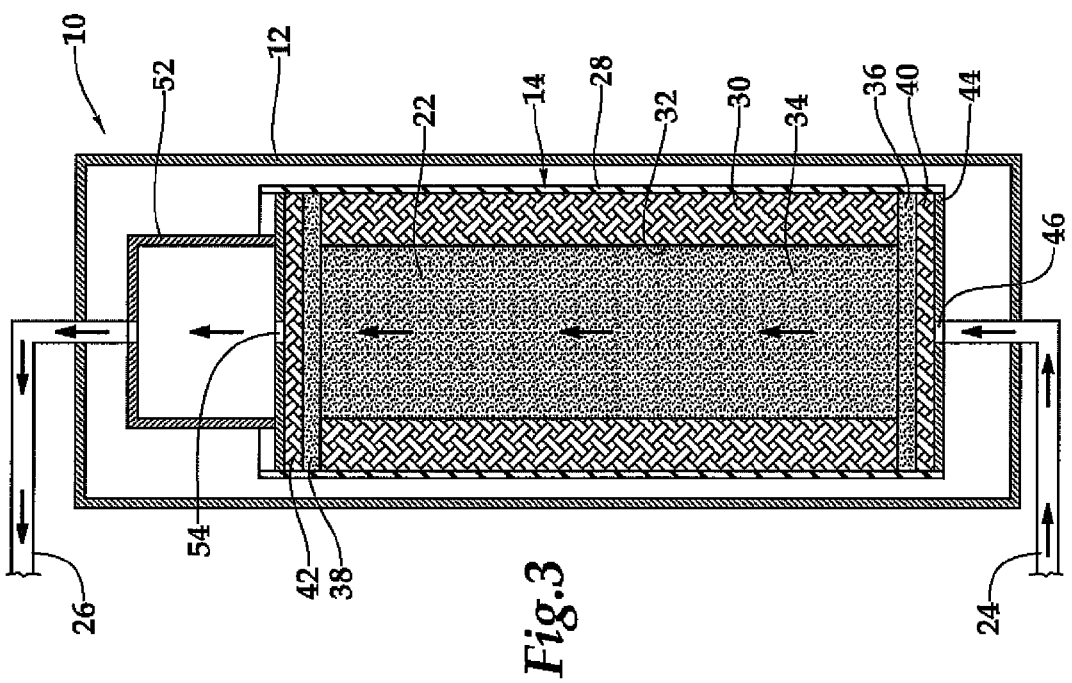
FIG. 3 is a schematic illustration of an apparatus for constructing a target core to enable testing at simulated wellbore conditions embodying principles of the present invention in a flow test configuration prior to perforating the target core.

Once apparatus 10 is in the above configuration, target assembly 14 may be used to place unconsolidated sand 34 in simulated wellbore conditions to form target core 22. As best seen in FIG. 3, if it is desired to run flow tests with target core 22 prior to perforating target core 22, then simulated wellbore 52 having opening 54 is placed relative to end plate 42. Target assembly 14 may then be placed in pressure vessel 12 and connected to the flow system such that confining pressure may be applied to target core 22. Confining pressure, such as 3,000 psi, is applied by pressurizing pressure vessel 12. This pressure acts on the exterior of flexible jacket 28. Flexible jacket 28 transmits a radial confining force to support core 30. Support core 30 in turns applies at least a portion of the confining force to target core 22. In this configuration, flow testing may be performed on target core 22 by pumping a desired fluid through the flow system as indicate by the arrows in FIG. 3.

In the illustrated embodiment, the fluid is pumped from inlet tubing 24 through opening 46 of flow distributor plate 44, end plate 40, unconsolidated sand layer 36, target core 22, unconsolidated sand layer 38, end plate 42, simulated wellbore 52 via opening 54 and into outlet tubing 26. During the flow testing, a variety of sensors are used to gather data. For example, parameters such as the confined pressure in target core 22 and support core 30, the pressure in simulated wellbore 52, the pore pressure, the fluid temperature in inlet tubing 24, the flow rate through target core 22 and the like will be measured. Based upon these and other measurements that those skilled in the art will take, a determination of factors such as porosity, permeability, pore volume compressibility of target core 22 under various simulated wellbore conditions can be made. These values can be used to calculate the expected flow into a perforation made in target core 22, as described below. In addition to these target core 22 measurements, other flow testing regimens may be performed to determine properties such as relative permeability, capillary pressure, critical velocity, wettability, electrical properties and core-log correlations. In addition fluid compatibility testing may be performed to determine sensitivity to certain fluids such as completion fluids and treatment fluids including chemicals, gels, resins and injection waters. Further, improved recovery mechanisms may be tested including thermal or steam testing and miscible injections as well as testing with foams or gases.

Independent of or following the flow testing, apparatus 10 may be configured for perforating target core 22. As best seen in FIG. 1, cement coupon 48 is placed on end plate 42. Cement coupon 48 is used to simulate the cement that surrounds the wellbore in the downhole environment. Accordingly, cement coupon 48 is preferably about three quarters of an inch thick. Placed on top of cement coupon 48 is casing plate 50 that is used to simulate the wellbore casing downhole. As such, casing plate 50 is preferably a three eighths inch thick plate of steel. Next, simulated wellbore 16 is positioned on top of casing plate 50. Disposed within simulated wellbore 16 is gun assembly 18 including shaped charge 20. In this configuration, suitable standoff is established between shaped charge 20 and casing plate 50 to simulate the wellbore environment.

Once apparatus 10 is in this configuration, confining pressure, wellbore pressure and pore pressure may be applied to target core 22. As described above, confining pressure, such as 3,000 psi, is applied by pressurizing pressure vessel 12. This pressure acts on the exterior of flexible jacket 28. Flexible jacket 28 then transmits a radial confining force to support core 30. Support core 30 in turns applies at least a portion of the confining force to target core 22. Wellbore pressure is applied by pressurizing simulated wellbore 16 to a desired pressure, for example, 500 psi. This pressure may be established using fluid within the flow system or via an independent pressure source that may include a fluid accumulator or other pressure ballast of at least one gallon capacity that can be precharged to one half the intended wellbore pressure. The flow system applies pore pressure to target core 22. For example, the pore pressure may be about 1,000 psi. Preferably, the confining pressure, the wellbore pressure and the pore pressure are brought simultaneously to the desired levels.

In this configuration, 3,000 psi confining stress, 500 psi wellbore pressure and 1,000 psi pore pressure, the effective rock stress or net confining stress is 2,000 psi, the overburden is 3,000 psi and there is a 500 psi underbalance. Gun assembly 18 may now be used to detonate shaped charge 20 to form a perforation in target core 22. As best seen in FIG. 4, upon detonation, a jet formed from shaped charge 20 penetrates into target core 22 forming opening 56 in casing plate 50, opening 58 in cement coupon 48, opening 60 in end plate 42, opening 62 in unconsolidated sand layer 38 and perforation 64 in target core 22. Once perforation 64 has been formed, the pore pressure is maintained or adjusted to initiate flow through target core 22. Once flow is established, as indicate by the arrows in FIG. 4, at least ten liters of fluid may be flowed through target core 22 at this pressure. Preferably, however, fluid is allowed to flow through target core 22 until no further change in flow rate occurs. Thereafter, any number and type of flow tests, such as those discussed above, may be performed.

Following flow testing, apparatus 10 is disassembled and target core 22 may be cut along its axial axis such that characteristics of the perforation can be determined. For example, the debris-free depth, i.e., the measured distance from rock face to the first debris in the hole, may be measured with a blunt probe. The total core penetration, i.e., the distance from rock face to deepest effect of penetration, may be measured with by probing for weakened rock beyond the perforation tip. The perforation diameter profile may be determined by measuring the diameter of the perforation at one inch intervals along the length of the perforation.

Through use of the apparatus 10 of the present invention, performance data may be gathered for various shaped charges that are use to perforate target cores formed from unconsolidated sand having various characteristics under various simulated wellbore conditions. Specifically, the following data is preferably obtained prior to and during flow testing and perforation of target core 22: target core source, diameter, length, orientation and fluid saturation; target core permeabilities; test conditions during both shooting and flowing; perforation geometry; differential pressure and flow rate at one-liter intervals, differential pressure and flow rate used in calculating maximum flow rate and cumulative flow; inlet temperature of fluid used and corresponding viscosity and the like.

Through use of this data, a variety of performance parameters may be determined. For example, core flow efficiency, which is a ratio of observed flow to calculated flow may be determined. In this analysis, calculated flow is established based upon factors including measured debris free perforation depth, average perforation diameter, initial permeability and applied pressure boundary conditions. The core flow efficiency as well as other factors that are identifiable through the use of the present invention in association with unconsolidated sands now enables the benefits of Section IV testing procedures to be extended to reservoirs in unconsolidated sands.

While this invention has been described with a reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An apparatus for constructing a target core to enable testing at simulated wellbore conditions, the apparatus comprising:
    a support core having a target core receiving region;
    a flexible jacket operable to receive the support core and apply a confining stress to the support core; and
    a quantity of unconsolidated sand disposed within the target core receiving region of the support core,
    wherein the support core is operable to transmit at least a portion of the confining stress to the unconsolidated sand thereby forming the target core from the unconsolidated sand.

2. The apparatus as recited in claim 1 wherein the support core, the target core and the flexible jacket are each substantially cylindrical.

3. The apparatus as recited in claim 1 wherein the support core is formed from a consolidated sandstone.

4. The apparatus as recited in claim 3 wherein the consolidated sand is selected from Castlegate sandstone, Berea sandstone and synthetic sandstone.

5. The apparatus as recited in claim 1 wherein the support core has a compressive strength between about 1,000 psi and about 12,000 psi.

6. The apparatus as recited in claim 1 wherein the flexible jacket further comprises a rubber sleeve.

7. The apparatus as recited in claim 1 wherein the confining stress further comprises a radial confining stress created by applying pressure to the exterior of the flexible jacket.

8. The apparatus as recited in claim 1 further comprising first and second unconsolidated sand layers and first and second end plates positioned at first and second ends of the support core, the first and second unconsolidated sand layers, respectively, in contact with first and second ends of the target core.

9. The apparatus as recited in claim 8 wherein the first and second end plates are formed from the same material as the support core.

10. The apparatus as recited in claim 8 further comprising a flow distributor plate positioned adjacent to the first end plate and opposite the first unconsolidated sand layer.

11. The apparatus as recited in claim 10 further comprising a cement coupon positioned adjacent to the second end plate and opposite the second unconsolidated sand layer and a casing plate positioned adjacent to the cement coupon and opposite the second end plate.

12. The apparatus as recited in claim 11 wherein an axial confining stress is applied to the target core created by applying pressure to the casing plate and the flow distributor plate.

13. The apparatus as recited in claim 11 further comprising a gun assembly operably positioned relative to the casing plate, the gun assembly including a shaped charge operable to form a perforation in the target core under the simulated downhole conditions.

14. An apparatus for constructing a target core to enable testing at simulated wellbore conditions, the apparatus comprising:
a support core having a target core receiving region and first and second ends;
a flexible jacket operable to receive the support core and apply a confining stress to the support core;
a quantity of unconsolidated sand disposed within the target core receiving region of the support core;
first and second unconsolidated sand layers positioned at the first and second ends of the support core such that the first and second unconsolidated sand layers, respectively, contact first and second ends of the unconsolidated sand disposed within the target core receiving region;
first and second end plates positioned adjacent to the first and second unconsolidated sand layers;
a flow distributor plate positioned adjacent to the first end plate and opposite the first unconsolidated sand layer;
a cement coupon positioned adjacent to the second end plate and opposite the second unconsolidated sand layer;
a casing plate positioned adjacent to the cement coupon and opposite the second end plate; and
a gun assembly operably positioned relative to the casing plate, the gun assembly including a shaped charge,
wherein the support core is operable to transmit at least a portion of the confining stress to the unconsolidated sand thereby forming the target core from the unconsolidated sand such that detonation of the shaped charge to form a perforation in the target core occurs under the simulated downhole conditions.

15. The apparatus as recited in claim 14 wherein the support core, the target core and the flexible jacket are each substantially cylindrical.

16. The apparatus as recited in claim 14 wherein the support core is formed from a consolidated sandstone selected from Castlegate sandstone, Berea sandstone and synthetic sandstone.

17. The apparatus as recited in claim 14 wherein the support core has a compressive strength between about 1,000 psi and about 12,000 psi.

18. The apparatus as recited in claim 14 wherein the flexible jacket further comprises a rubber sleeve.

19. The apparatus as recited in claim 14 wherein the confining stress further comprises a radial confining stress and an axial confining stress created by applying pressure to the exterior of the flexible jacket, the casing plate and the flow distributor plate.

20. A method for constructing a target core to enable testing at simulated wellbore conditions, the method comprising:
providing a support core having a target core receiving region;
positioning the support core in a flexible jacket;
disposing a quantity of unconsolidated sand within the target core receiving region of the support core;
applying a confining stress to the support core; and
transmitting at least a portion of the confining stress to the unconsolidated sand thereby forming the target core from the unconsolidated sand.

21. The method as recited in claim 20 wherein the support core is formed from a consolidated sandstone selected from Castlegate sandstone, Berea sandstone and synthetic sandstone.

22. A method for perforating a target core at simulated wellbore conditions, the method comprising:
providing a support core having a target core receiving region;
positioning the support core in a flexible jacket;
disposing a quantity of unconsolidated sand within the target core receiving region of the support core;
applying a confining stress to the support core;
transmitting at least a portion of the confining stress to the unconsolidated sand thereby forming the target core from the unconsolidated sand; and
detonating a shaped charge positioned relative to the target core to form a perforation in the target core under the simulated downhole conditions.

23. The method as recited in claim 22 wherein the support core is formed from a consolidated sandstone selected from Castlegate sandstone, Berea sandstone and synthetic sandstone.

24. A method for performance testing of a perforation in a target core at simulated wellbore conditions, the method comprising:
providing a support core having a target core receiving region;
positioning the support core in a flexible jacket;
disposing a quantity of unconsolidated sand within the target core receiving region of the support core;
applying a confining stress to the support core;

transmitting at least a portion of the confining stress to the unconsolidated sand thereby forming the target core from the unconsolidated sand;

flowing a first fluid sample axially through the target core;

detonating a shaped charge positioned relative to the target core to form a perforation in the target core under the simulated downhole conditions; and flowing a second fluid sample axially through the target core.

25. The method as recited in claim 24 wherein measured parameters associated with flowing the first fluid sample and the second fluid sample are compared to determine flow performance of the perforation.

* * * * *